(12) United States Patent  
Kozloski

(10) Patent No.: US 8,296,072 B2  
(45) Date of Patent: Oct. 23, 2012

(54) TECHNIQUES FOR RECORDING SIGNALS

(75) Inventor: James R. Kozloski, New Fairfield, CT (US)

(73) Assignee: International Business Machines Corporation, Armonk, NY (US)

( * ) Notice: Subject to any disclaimer, the term of this patent is extended or adjusted under 35 U.S.C. 154(b) by 393 days.

(21) Appl. No.: 12/208,900

(22) Filed: Sep. 11, 2008

(65) Prior Publication Data

US 2009/0029384 A1  Jan. 29, 2009

Related U.S. Application Data

(63) Continuation of application No. 10/640,119, filed on Aug. 13, 2003, now abandoned.

(51) Int. Cl.
*G06F 7/00* (2006.01)

(52) U.S. Cl. ............... 702/19; 702/20; 703/11; 707/700

(58) Field of Classification Search ........................ None
See application file for complete search history.

(56) References Cited

U.S. PATENT DOCUMENTS

| | | | |
|---|---|---|---|
| 5,912,137 A | 6/1999 | Tsien et al. | 435/15 |
| 5,925,558 A | 7/1999 | Tsien et al. | 435/252.3 |
| 5,948,906 A | 9/1999 | Tsien et al. | 540/467 |
| 5,981,200 A | 11/1999 | Tsien et al. | 435/7.4 |
| 5,998,204 A | 12/1999 | Tsien et al. | 435/325 |
| 6,008,378 A | 12/1999 | Tsien et al. | 549/207 |
| 6,046,925 A | 4/2000 | Tsien et al. | 365/111 |
| 6,054,271 A | 4/2000 | Tsien et al. | 435/6 |
| 6,054,321 A | 4/2000 | Tsien et al. | 436/86 |
| 6,066,476 A | 5/2000 | Tsien et al. | 435/69.7 |
| 6,077,707 A | 6/2000 | Tsien et al. | 435/325 |
| 6,107,066 A | 8/2000 | Tsien et al. | 435/173.4 |
| 6,124,128 A | 9/2000 | Tsien et al. | 435/252.33 |
| 6,140,132 A | 10/2000 | Tsien et al. | 436/86 |
| 6,150,176 A | 11/2000 | Tsien et al. | 436/86 |
| 6,180,411 B1 | 1/2001 | Tsien et al. | 436/79 |
| 6,197,928 B1 | 3/2001 | Tsien et al. | 530/350 |
| 6,248,550 B1 | 6/2001 | Tsien et al. | 435/15 |
| 6,319,669 B1 | 11/2001 | Tsien et al. | 435/6 |
| 6,342,379 B1 | 1/2002 | Tsien et al. | 435/173.4 |
| 6,349,160 B2 | 2/2002 | Tsien et al. | 385/35 |
| 6,403,374 B1 | 6/2002 | Tsien et al. | 435/325 |
| 6,469,154 B1 | 10/2002 | Tsien et al. | 536/23.5 |
| 2002/0141321 A1 | 10/2002 | Wada et al. | 369/112.18 |
| 2004/0038241 A1 | 2/2004 | Glennsbjerg | 435/6 |
| 2005/0153320 A1 | 7/2005 | Herron et al. | 435/6 |

FOREIGN PATENT DOCUMENTS

| | | |
|---|---|---|
| JP | 01322623 A | 5/1991 |
| JP | 2001266407 A | 9/2001 |
| JP | 2004326906 A | 11/2006 |

OTHER PUBLICATIONS

Wright, B.E., "A Biochemical Mechanism for Nonrandom Mutations and Evolution," Journal of Bacteriology, vol. 182, No. 11, pp. 2993-3001 (Jun. 2000).
Zhou et al., "The Effect of Ribavirin and IMPDH Inhibitors on Hepatitis C Virus Subgenomic Replicon RNA," Virology, vol. 310, No. 2, pp. 333-342 (Jun. 5, 2003).
Hodgkin et al., "Measurement of Current-Voltage Relations in the Membrane of the Giant Axon of LOLIGO," J. Physiol., 116, 424-448 (1952).
Jacobs et al., "Complementary Emerging Techniques: High-Resolution PET and MRI," New Technologies, pp. 621-629.
Kralik et al., "Techniques for Long-Term Multisite Neuronal Ensemble Recordings in Behaving Animals," Methods 25, 121-150 (2001).
Majewska et al., "Instruments and Techniques: A Custom-Made Two-Photon Microscope and Deconvolution System," Pflugers Archiv—European Journal of Physiology, pp. 1-22 (2000).
Smetters et al.. "Detecting Action Potentials in Neuronal Populations with Calcium Imaging," Methods: A Companion to Methods in Enzymology 18, 215-221 (1999).

*Primary Examiner* — Mary Zeman
(74) *Attorney, Agent, or Firm* — Ryan, Mason & Lewis, LLP

(57) ABSTRACT

The present invention provides techniques of recording signals. In one aspect of the invention, a method of recording a signal comprises the following steps. One or more errors are selectively introduced during synthesis of a polymer in response to the signal. The one or more occurrences of the one or more errors in the synthesized polymer are recorded. The synthesis of the polymer may comprise a polymer synthetase that can selectively introduce the one or more errors in response to the signal. A method for analyzing signals is also provided.

23 Claims, 1 Drawing Sheet

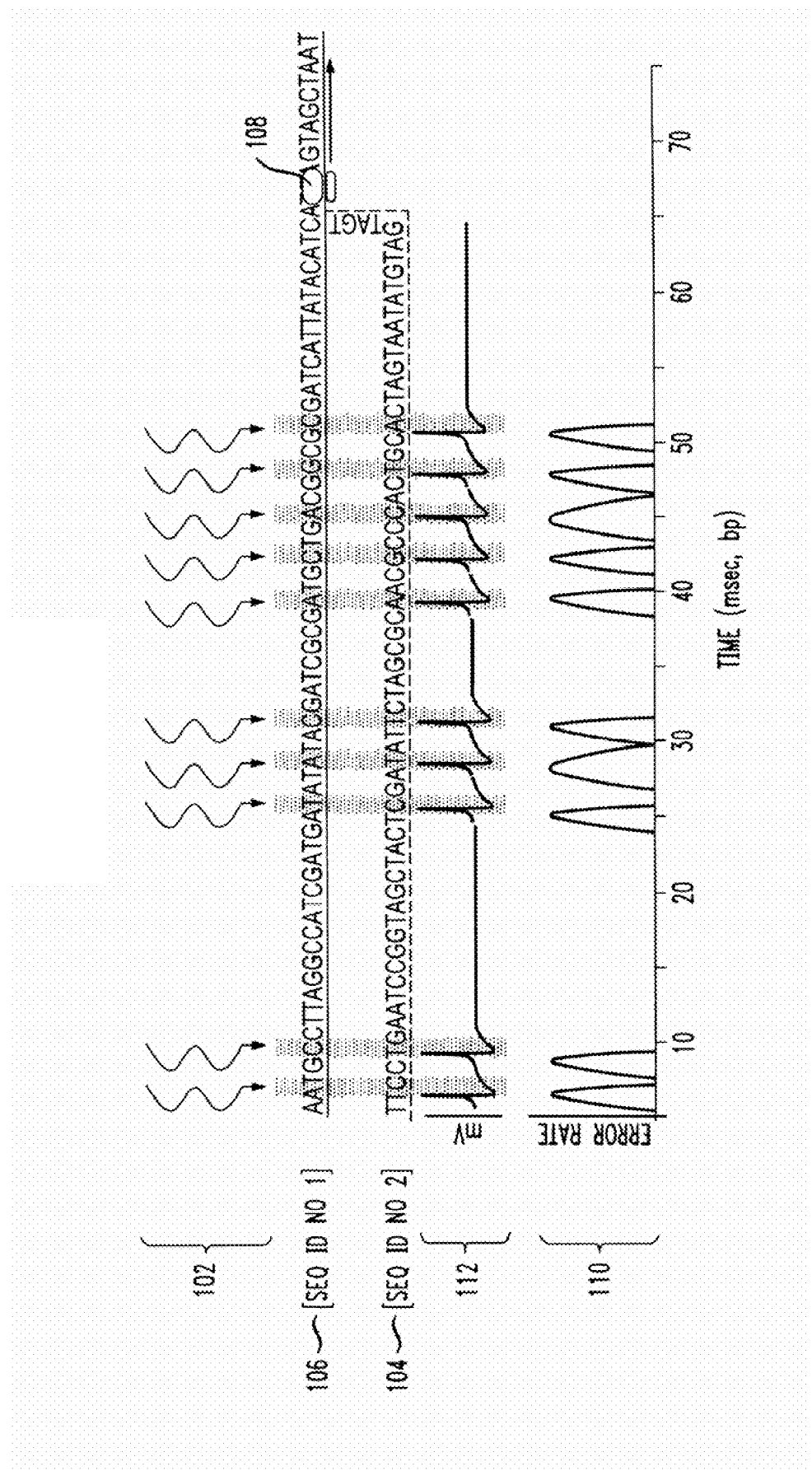

TECHNIQUES FOR RECORDING SIGNALS

CROSS-REFERENCE TO RELATED APPLICATIONS

This application is a continuation of U.S. patent application Ser. No. 10/640,119, filed Aug. 13, 2003, incorporated by reference herein.

FIELD OF THE INVENTION

The present invention relates to signals and, more particularly, to techniques for recording and analyzing signals.

BACKGROUND OF THE INVENTION

Recording intracellular signals is a key source of data in the fields of genomics, cell biology and neuroscience. For example, in genomics and cell biology, patterns of gene expression and protein interactions are measured by monitoring concentrations of key molecules within the cell. In neuroscience, recordings of voltage differences across a cell membrane or of concentrations of free ions provide investigators access to the temporal pattern of intracellular action potentials (one millisecond, 100 millivolt (mV) pulses) with which nearly all computation in the brain is performed.

Biological organisms are composed of various structures, which are composed of large numbers of cells of a wide variety of types. For example, the nervous system is composed of billions of cells, i.e., neurons, that communicate using patterns of action potentials relayed across anatomically specified connections. Traditional methods for recording from a neuron involve accessing the intracellular space of the neuron at a point where it is on the order of about ten to about 25 micrometers in diameter, with a glass microelectrode, amplifying the voltage difference between the inside and outside of the cell and recording the amplified signal using a recording device. For a description of a method involving accessing the intracellular space of a neuron, see A. L. Hodgkin et al., *Measurement of Current-Voltage Relations in the Membrane of the Giant Axon of Loligo*, J. PHYSIOL., 116, 424-448 (1952). Accessing multiple neurons requires the use of multiple electrodes, each connected to a separate amplifier and recording device. The mechanical constraints on recording from such small biological structures have limited the proximity and number of recordings that can be made simultaneously. Even though advances have expanded capabilities to allow for the recording of larger numbers of neurons, constraints still exist. Current techniques are limited to recording up to only one hundred neurons simultaneously. See J. D. Kralik et al., *Techniques for Long-Term Multisite Neuronal Ensemble Recordings in Behaving Animals*, 25 METHODS, 121-51 (2001).

To fully characterize a biological structure, recordings from a large number of cells are required. These recordings need to be analyzed off-line to determine temporal correlations, cause and effect interactions and potential communication and information processing strategies implemented by the structure. Due to the limitations on the number of simultaneous recordings currently possible, recordings from different experiments, performed at different times, and on different specimens, are combined to conduct these off-line analyses. Combining results from different experiments can often obscure the underlying dynamics of any one of the experimental preparations studied and therefore lead to incorrect conclusions, e.g., regarding the overall function of a structure.

An alternate approach for intracellular recording involves the use of optical methods in which intracellular signals are translated into fluorescence signals via an artificially introduced intracellular fluorophore. See D. Smetters et al., *Detecting Action potentials in Neuronal Populations with Calcium Imaging*, 18 METHODS 215-221. These optical methods solve the problem of mechanically accessing the intracellular spaces of multiple cells simultaneously since the light emitted from cells under fluorescent illumination is recorded using microscopic video recordings. However, most biological tissue is highly light-scattering, so resolution of single cells becomes impossible as the focal plane advances to only one millimeter (mm) inside a structure, even when the most advanced microscopic techniques are employed to collect the emitted light. Furthermore, the field of view and numerical aperture of the light collecting apparatus limits the size of a structure that can be imaged, and thus the number of cells that can be recorded simultaneously using these methods. Chimeric fluorescent proteins have been synthesized that monitor cellular signals. However, they do not overcome the shortcomings highlighted above.

Another alternative approach for recording signals from cells involves the use of functional magnetic resonance imaging (fMRI) or positron emission tomography (PET). Both methods can record from very large regions of brain tissue. The spatial resolution of these methods is limited to millimeter-scale, however, and the temporal resolution to hundreds of milliseconds. Therefore, intracellular recordings of action potentials using either of these methods are theoretically impossible, given the much smaller size of single neurons, e.g., less than 0.05 mm, and much briefer time-scale of the action potential, e.g., about one millisecond. Instead, what fMRI and PET imaging provide is access to an average signal from hundreds of thousands of adjacent neurons. While these recordings can be highly informative about brain function, they cannot decompose brain structures to the level of the single neuron, and thus cannot analyze neural computation within these structures.

It would be desirable to have a technique for cellular analysis that does not suffer from the above and other limitations, such that comprehensive study of biological structures and processes may be realized.

SUMMARY OF THE INVENTION

The present invention provides techniques of recording signals. In one aspect of the invention, a method of recording a signal comprises the following steps. One or more errors are selectively introduced during synthesis of a polymer in response to the signal. The one or more occurrences of the one or more errors in the synthesized polymer are recorded. The synthesis of the polymer may comprise a polymer synthetase that can selectively introduce the one or more errors in response to the signal.

In another aspect of the invention, a method of analyzing signals comprises the following steps. From a plurality of sources, a plurality of signals are simultaneously recorded. The plurality of signals are recorded by selectively introducing one or more errors during synthesis of polymers in response to the plurality of signals and recording one or more occurrences of the one or more errors in the synthesized polymers. The one or more recorded occurrences of the one or more errors for the plurality of sources are compared.

A more complete understanding of the present invention, as well as further features and advantages of the present invention, will be obtained by reference to the following detailed description and drawing.

BRIEF DESCRIPTION OF THE DRAWING

FIG. 1 is a diagram illustrating an exemplary technique of recording a cellular signal according to an embodiment of the present invention.

DETAILED DESCRIPTION OF PREFERRED EMBODIMENTS

The present invention will be described below in the context of an illustrative technique for recording and analyzing cellular signals. However, it is to be understood that the teachings of the present invention are not to be limited to signals associated with cells, but are intended to also include signals derived from other sources, for example, non-biological sources.

FIG. 1 is a diagram illustrating an exemplary technique of recording a cellular signal. Errors may be selectively introduced during the synthesis of a polymer, in this exemplary embodiment a biopolymer, in response to a cellular signal, as shown in FIG. 1. Specifically, in FIG. 1, cellular signals 102 are present. Cellular signals 102 may comprise any occurrence that is indicative of a particular cellular activity, including, but not limited to, calcium concentrations, cyclic adenosine monophosphate (cAMP) concentrations, cyclic guanosine monophosphate (cGMP) concentrations, voltage, pH and any combination comprising at least one of the foregoing cellular signals. Thus, the term cellular signal, as used herein, broadly relates to any indicators of cellular activity. As such, cellular signals 102 may be correlated with cellular activity. For example, when cellular signals 102 comprise calcium concentrations, the correlated cellular activity might be a nerve impulse. During a nerve impulse, elevated calcium concentrations arise when voltage-gated calcium channels open, which can lead to the release of neurotransmitters that transmit the nerve impulse from one neuron to another.

The cellular signals recorded herein may comprise either intracellular signals, extracellular signals or both. Namely, the techniques provided herein are equally applicable to recording intracellular signals indicative of correlated intracellular activity as to signals existing extracellularly or independently via an in vitro medium wherein, for example, the cellular signal and biopolymer synthesis precursors are artificially provided, as is described in detail below.

The biopolymer synthesized, e.g., biopolymer 104, may comprise any biological material comprising a chain of subunits, the composition of which may be obtained by conventional methods, such as by sequencing technology, and the synthesis of which may be controlled and monitored. Suitable biopolymers include biological materials, including, but not limited to, deoxyribonucleic acid (DNA), ribonucleic acid (RNA), DNA derivatives, RNA derivatives, proteins, carbohydrates and combinations comprising at least one of the foregoing biopolymers. In an exemplary embodiment, biopolymer 104 comprises DNA.

In the exemplary embodiment shown in FIG. 1, biopolymer 104 is synthesized using a template strand, namely biopolymer 106, according to the known processes of DNA replication. Biopolymer 106 may then also comprise any biological materials, including, but not limited to, DNA, RNA, DNA derivatives, RNA derivatives, proteins, carbohydrates and combinations comprising at least one of the foregoing biopolymers. As such, biopolymer 104 and biopolymer 106 will be complementary materials. The use of complementary materials for biopolymer synthesis, e.g., replication or transcription, as shown in FIG. 1, however, is only one exemplary methodology. Biopolymers may be synthesized by other known biochemical mechanisms that will dictate what the composition, the sequence of subunits, in the biopolymer should be, resulting in a predictable sequence of elements. According to the teachings herein, the biopolymer synthesis methodology employed should result in a predictable sequence of subunits to enable determination of the errors introduced, as is described in detail below. These biochemical mechanisms may involve use of certain precursors and metabolic pathways to orchestrate synthesis of a biopolymer.

Errors selectively introduced during synthesis of biopolymer 104 are then identified. The term "errors," as used herein, refers to any unexpected subunit occurring within the biopolymer. An expected sequence of subunits in the biopolymer may be predicted based on known biochemical processes. These processes may include the replication or transcription of one biopolymer into another, in which case, the expected sequence of subunits is represented by the template or complementary biopolymer. Other known biochemical processes can generate expected sequences based on predicted sequences without a template necessarily existing, as described above.

In the instance wherein the expected sequence of subunits is represented by a complementary biopolymer, e.g., biopolymer 106, the composition of the complementary biopolymer should be known, or be determinable. The composition of biopolymer 104 that is synthesized may then be compared with the known or determined composition of biopolymer 106, as will be described in detail below.

In an exemplary embodiment, errors are selectively introduced during synthesis of biopolymer 104 through use of an engineered biopolymer synthetase, e.g., biopolymer synthetase 108, that is responsive to cellular signals 102. Biopolymer synthetase 108 may comprise any biopolymer synthesis catalyst, including, but not limited to, a polymerase, such as DNA polymerase or RNA polymerase. However, the term "synthetase," as used herein, is broadly applicable to any molecules that catalyze the linkage of at least two molecules.

The error rate of biopolymer synthetase 108 increases as a result of the presence of cellular signals 102. For example, when calcium concentrations increase, the replication error rate increases. As the cellular signals 102 reach saturation, the error rate should ideally approximate one error per subunit. With a low inherent error rate, as is described below, an error in the synthesized sequence can, with relative certainty, be attributed to cellular signals 102.

Biopolymer synthetases play an important role in many bodily processes, including the replication of genetic material. For example, copies of DNA are produced by a type of biopolymer synthetase protein, namely, a DNA polymerase that constructs complementary DNA strands from a particular template sequence. In an exemplary embodiment, the biopolymer synthesized is DNA and the biopolymer synthetase is DNA polymerase. However, according to the teachings herein, the biopolymer may comprise any suitable genetic material, such as RNA, and the biopolymer synthetase may comprise any suitable biopolymer synthetase, such as RNA polymerase.

Synthesis of biopolymers such as DNA and RNA occurs at rates approaching 1,000 base pairs per second (bp/sec). During the natural replication process, inherent errors do occur. The rate of occurrence of these inherent errors (the inherent error rate) is however typically very low. The inherent error rate is generally less than $1 \times 10^{-5}$ errors per subunit. For example, for T7 viral DNA replication, the error rate is about $1 \times 10^{-7}$ errors per subunit, whereas the error rate for *Escherichia coli* and *Drosophila melanogaster* is about $1 \times 10^{-1}$ errors per subunit. As mentioned above, however, with an engineered biopolymer synthetase, e.g., biopolymer synthetase 108, error rates may approximate one error per subunit during the presence of cellular signals 102. Thus, according to the teachings herein, when cellular signals 102 are not present, the engineered biopolymer synthetase should exhibit an error rate that approximates the inherent error rate of the natural protein, e.g., less than $1 \times 10^{-5}$ errors per subunit.

The error rate of biopolymer synthetase 108 may be increased in response to cellular signals 102 by any suitable mechanism that allows reversion back to the inherent error rate once an amount of cellular signals 102 is reduced or absent. In an exemplary embodiment, the presence of cellular signals 102 induces a conformational change in biopolymer synthetase 108. The conformational change causes biopolymer synthetase 108 to increasingly place incorrect subunits within synthesized biopolymer 104 at locatable positions in the biopolymer chain.

In the exemplary embodiment wherein biopolymer synthetase 108 comprises DNA polymerase, and biopolymer 104 comprises DNA, an incorrect subunit denotes a nucleotide base that is non-complementary to the nucleotide base at the same position on the complementary strand, i.e., biopolymer 106. For example as shown in FIG. 1, biopolymer 106 from the 5' end of the strand has the first three nucleotide bases adenine (A), adenine and thymine (T). Biopolymer 104 from the 5' end of the strand has the first three nucleotide bases thymine, thymine and cytosine (C). While adenine and thymine are complementary nucleotide base pairs, thymine and cytosine are not. Thus, the incorrect nucleotide base pairing of cytosine in biopolymer 104 is presumed to be in response to cellular signals 102.

Thus, for example, if cellular signals 102 comprise calcium concentrations, during a nerve impulse the calcium levels will rise and biopolymer synthetase 108 will undergo a temporary conformational change, and the error rate during replication will increase. This conformational change is generated by the binding of calcium to a calcium binding domain artificially introduced into the DNA polymerase protein using typical protein engineering techniques. Upon binding calcium, the modified protein undergoes a conformational change that renders inactive the epsilon subunit of the DNA polymerase, which is normally responsible for 3' to 5' exonuclease activity and the normal ability of the DNA polymerase to 'proofread' the replicated DNA. Replication will proceed at a normal rate because a second polymerization subunit of the DNA polymerase remains unaffected by the conformational change. Errors introduced by the polymerization subunit are no longer excised and corrected by the epsilon subunit, because the calcium-induced conformational change has rendered the epsilon subunit inactive.

Thus, the effective error rate for the modified DNA polymerase, e.g., biopolymer synthetase 108, and thus the error rate observed within the newly synthesized strand of DNA, will be higher whenever and wherever replication occurs in the presence of increased calcium concentrations. When calcium levels fall, the calcium binding domain no longer binds calcium, the modified DNA polymerase returns to its previous conformation, the proofreading function of the epsilon subunit of the DNA polymerase is restored and the inherent error rate is encountered.

Examples of engineered proteins capable of changing conformation and translating an intracellular signal into a recordable signal, such as a fluorescent signal, may be found, for example, in Tsien et al., U.S. Pat. No. 6,469,154, "Fluorescent Protein Indicators," Tsien et al., U.S. Pat. No. 6,403,374, "Long Wavelength Engineered Fluorescent Proteins," Tsien et al., U.S. Pat. No. 6,349,160, "Detector and Screening Device for Ion Channels," Tsien et al., U.S. Pat. No. 6,342,379, "Detection of Transmembrane Potentials by Optical Methods," Tsien et al., U.S. Pat. No. 6,319,669, "Modified Green Fluorescent Proteins," Tsien et al., U.S. Pat. No. 6,248,550, "Assays for protein kinases using fluorescent protein substrates," Tsien et al., U.S. Pat. No. 6,197,928, "Fluorescent Protein Sensors for Detection of Analytes," Tsien et al., U.S. Pat. No. 6,180,411, "Light-Triggered Indicators That Memorize Analyte Concentrations," Tsien et al., U.S. Pat. No. 6,150,176, "Fluorescent Protein Sensors for Measuring the pH of a Biological Sample," Tsien et al., U.S. Pat. No. 6,140,132, "Fluorescent Protein Sensors for Measuring the pH of a Biological Sample," Tsien et al., U.S. Pat. No. 6,124,128, "Long Wavelength Engineered Fluorescent Proteins," Tsien et al., U.S. Pat. No. 6,107,066, "Detection of Transmembrane Potentials by Optical Methods," Tsien et al., U.S. Pat. No. 6,077,707, "Long Wavelength Engineered Fluorescent Proteins," Tsien et al., U.S. Pat. No. 6,066,476, "Modified Green Fluorescent Proteins," Tsien et al., U.S. Pat. No. 6,054,321, "Long Wavelength Engineered Fluorescent Proteins," Tsien et al., U.S. Pat. No. 6,054,271, "Methods of Using Synthetic Molecules and Target Sequences," Tsien et al., U.S. Pat. No. 6,046,925, "Photochromic Fluorescent Proteins and Optical Memory Storage, Devices Based on Fluorescent Proteins," Tsien et al., U.S. Pat. No. 6,008,378, "Synthetic Molecules That Specifically React With Target Sequences," Tsien et al., U.S. Pat. No. 5,998,204, "Fluorescent Protein Sensors for Detection of Analytes," Tsien et al., U.S. Pat. No. 5,981,200, "Tandem Fluorescent Protein Constructs," Tsien et al., U.S. Pat. No. 5,948,906, "Fluorescent Indicator Dyes for Alkali Metal Cations," Tsien et al., U.S. Pat. No. 5,925,558, "Assays for Protein Kinases Using Fluorescent Protein Substrates," Tsien et al., U.S. Pat. No. 5,912,137, "Assays for Protein Kinases Using Fluorescent Protein Substrates," the disclosures of which are incorporated by reference herein. The engineered proteins provided therein provide a fluorescence-based analysis.

In an exemplary embodiment, the techniques provided herein are performed in vivo, for example, in a murine, i.e., mouse model with biopolymer synthetase 108 comprising DNA polymerase and biopolymer 104 comprising DNA. Biopolymer 106 and biopolymer synthetase 108 are introduced to a mouse host (hereinafter "the host"). Biopolymer 106 and biopolymer synthetase 108 may be introduced to the host by any suitable known techniques, including, but not limited to, viral infection, direct injection with cells, use of transgenic hosts already comprising biopolymer 106 and biopolymer synthetase 108 and combinations comprising at least one of the foregoing introduction techniques.

A plurality of cellular signals from a plurality of cells may be simultaneously recorded. To achieve an accurate temporal determination correlating cellular signals 102 and errors introduced in biopolymer 104, it is favorable to have control over the synthesis of biopolymer 104. Specifically, being able to control when the synthesis of biopolymer 104 begins, and ends, will give an accurate snapshot of a period during which cellular signals 102 occur and errors are introduced. In an exemplary embodiment, biopolymer synthetase 108 is introduced to the host in an inactive form. When desired, biopolymer synthetase 108 may be activated to begin replication of biopolymer 106. Specifically, biopolymer synthetase 108 may be selectively activated using drugs introduced into the host, some suitable external influences, including, but not limited to, heat-shock or any combination comprising at least one of the foregoing activation techniques.

Additionally, cellular signals 102 and/or correlated cellular activity may be invoked by some stimuli. Exemplary stimuli include external stimuli to which the host is exposed to, including, but not limited to, visible stimuli, audible stimuli and combinations comprising at least one of the foregoing stimuli. These stimuli are most applicable when cellular signals 102 correlate with a cellular activity comprising a nerve impulse. The host organism may also be stimulated with a particular drug. This drug introduction method is suitable for examining the systemic effects of a particular drug therapy.

Occurrences of the errors in the synthesis of biopolymer 104 are recorded, as further shown in FIG. 1. In FIG. 1, error rates 110 are shown in relation to cellular signals 102, biopolymer 106 and biopolymer 104. As can be seen from error rates 110, when each of cellular signals 102 are encountered, and subsequent incorrect subunits, e.g., nucleotide bases, appear in synthesized biopolymer 104, the error rate increases. Once that particular cellular signal is no longer present, the error rate 110 drops back down until another of cellular signals 102 is encountered.

As shown in FIG. 1, the synthesis of biopolymer 104 and the correlated error rate 110 are presented as a function of time. As was highlighted above, DNA replication occurs at a rate of about 1,000 bp/sec. As such, the techniques herein may comprise a duration dictated by, for example, the size of the genome being replicated. For example, if biopolymer 106 is a 40,000 base pair T7 viral genome, the experimental phase should not exceed 40 seconds. However, as the size of the genome used increases, the duration of the experimental phase may also increase.

To record the errors that occurred in the synthesis of biopolymer 104 once the predetermined duration of the experimental phase has been reached, the host is sacrificed and the tissue rapidly fixed. Sacrificing the host ceases further replication of biopolymer 106. The fixation step is necessary to preserve the synthesized biopolymer 104 in a stable state. The cell tissue of the host is then dissected and catalogued. The spatial resolution of the technique is determined at this phase. The spatial resolution can readily be reduced to single cell resolution given an appropriate dissection and retrieval method, for example, laser capture microdissection, see M. R. Emmert-Buck et al., *Laser Capture Microdissection*, 274 SCIENCE 5289, 998-1001 (1996).

Each cell may then be catalogued based on the physical coordinates indicating from where each cell was taken. Other information, including cell type, may be useful in cataloguing the cells.

Each of the synthesized biopolymers 104 are extracted from the cells and independently sequenced. The composition of each biopolymer 104 is then compared with a predicted composition, determined as described above. For example, as in FIG. 1, the composition of each biopolymer 104 may be compared with the sequences of each of the complementary biopolymers 106. Errors introduced during the synthesis of biopolymer 104 are identified and then may be analyzed. The errors in biopolymer 104 may be analyzed to correlate each error with the cellular signal 102 that presumably induced the error. Having a controlled experimental duration, e.g., fixed starting and stopping points, and a known rate of biopolymer synthesis allows for this correlation to be made with accuracy. FIG. 1 shows how this correlation can be used to further correlate cellular signals 102 with cellular activity. Correlating cellular signal 102 with cellular activity allows for analysis of the activities of cells both in relation to each other and to an overall system of such cells. In this exemplary embodiment, the cellular activities are nerve impulses. Nerve impulses, generally, are characterized by voltage fluctuations across the membranes of neurons, or nerve cells. As mentioned above, calcium concentrations may signal a nerve impulse. Using the information provided in FIG. 1, namely, when each instance of cellular signals 102 occurs and the error rates 110 during synthesis of biopolymer 104, the original cellular activity, e.g., nerve impulses 112, can be recreated.

According to the teachings herein, errors introduced during the synthesis of biopolymer 104 may be identified and analyzed using any conventional techniques. In an exemplary embodiment, errors are detected using a computer algorithm that operates upon the observed sequence of subunits and compares it to the predicted sequence of subunits. A predicted subunit in the observed sequence is recorded as a zero by the algorithm, and an unexpected subunit is recorded as a one. The recorded sequence of ones and zeros is then further processed by the algorithm, which might apply a filter to the sequence for the purpose of reconstructing the original cellular signal. This filter can be chosen from a set of common filters (e.g., a Gaussian filter) or can be computed and supplied to the algorithm for optimal reconstruction of the cellular signal. The plurality of reconstructed cellular signals are then compared by a second computer algorithm which performs correlation analyses to analyze cause and effect interactions and/or network properties that exist between the plurality of cells recorded. Correlations, cause and effect interactions and/or network properties are displayed by the second computer algorithm in relation to the catalogued position of the cell from which the cellular signal was recorded. In this manner, a spatio-temporal correlation map can be constructed.

As highlighted above, while the techniques provided herein are directed to experimental procedures with an in vivo model, it is to be understood that the techniques are equally applicable to in vitro experimentation. In an exemplary embodiment, biopolymer 106 and biopolymer synthetase 108 are introduced to a suitable medium containing the necessary precursors for the synthesis of biopolymer 104. Cellular signals 102 are selectively introduced and/or removed, and error rates 110, in the synthesis of biopolymer 104 are recorded.

As described above, the term signal may also include signals derived from non-biological sources. In an exemplary embodiment, the signals recorded may be chemical signals, e.g., from a chemical reaction. Production processes involving chemical reactions typically produce a chemical effluent. The presence of this chemical effluent may serve to selectively introduce errors during the synthesis of a polymer. As such, this chemical effluent may be a recordable and analyzable signal according to the techniques provided herein.

Although illustrative embodiments of the present invention have been described herein, it is to be understood that the invention is not limited to those precise embodiments, and that various other changes and modifications may be made by one skilled in the art without departing from the scope or spirit of the invention.

What is claimed is:

1. A method of recording a signal, the method comprising:
selectively introducing one or more errors during synthesis of an oligonucleotide based on the signal, wherein the recorded signal is based on one or more of calcium concentrations, cyclic AMP concentrations, cyclic GMP concentrations, voltage, and pH levels, and wherein the recorded signal is based on a cellular signal.

2. The method of claim 1, wherein the signal correlates with cellular activity.

3. The method of claim 1, wherein the signal correlates with a nerve impulse.

4. The method of claim 1, wherein an inherent error rate of the oligonucleotide synthesizer is known.

5. The method of claim 1, wherein synthesis of the polymer progresses at a known rate.

6. The method of claim 1, wherein the recorded signal is based on a recording performed in vitro.

7. The method of claim 1, wherein the recorded signal is based on a recording performed in vivo.

8. The method of claim 4, wherein the oligonucleotide synthesis introduces the one or more errors by a change in its inherent error rate induced by the signal during synthesis.

9. The method of claim 1, wherein the recording step further comprises the step of comparing an actual composition of the synthesized oligonucleotide with a predicted composition for the polymer.

10. The method of claim 9, wherein the predicted composition is derived from a complementary biopolymer.

11. The method of claim 1, further comprising the step of providing stimuli to induce the signal.

12. A method of analyzing signals, the method comprising:
simultaneously recording a plurality of signals from a plurality of sources by the steps of:
selectively introducing one or more errors during synthesis of oligonucleotides based on the plurality of signals, wherein the analyzed signal is based on one or more of calcium concentrations, cyclic AMP concentrations, cyclic GMP concentrations, voltage, and pH levels, and wherein each of the plurality of recorded signals is based on a cellular signal;
recovering one or more occurrences of the one or more errors in the synthesized oligonucleotides; and
comparing the one or more recovered occurrences of the one or more errors for the plurality of sources.

13. The method of claim 12, wherein the plurality of sources comprises one or more cells.

14. The method of claim 12, wherein the plurality of signals correlate with one or more cellular activities.

15. The method of claim 12, wherein the plurality of signals correlate with nerve impulses.

16. The method of claim 12, wherein an inherent error rate during synthesis of the oligonucleotide is known.

17. The method of claim 12, wherein synthesis of the oligonucleotide progresses at a known rate.

18. The method of claim 12, wherein the oligonucleotide synthesis introduces the one or more errors by a change in its inherent error rate.

19. The method of claim 12, wherein the recovery step further comprises the steps of:
comparing compositions of the synthesized oligonucleotide with expected compositions for the oligonucleotide;

identifying the one or more errors in the synthesized oligonucleotide; and analyzing the one or more errors.

20. The method of claim 19, wherein the expected compositions are derived from complementary DNA sequences.

21. The method of claim 1, wherein the error is introduced with a probability greater than the inherent error rate of the oligonucleotide synthesis.

22. A method of recovering a recorded signal, the method comprising:

sequencing one or more occurrences of one or more errors in an oligonucleotide; and comparing an actual composition of a synthesized oligonucleotide with an expected composition for the oligonucleotide to identify one or more errors that represent the recorded signal, wherein the recorded signal is based on one or more of calcium concentrations, cyclic AMP concentrations, cyclic GMP concentrations, voltage, and pH levels, and wherein the recorded signal is based on a cellular signal.

23. The method of claim 22, wherein the expected composition is derived from a complementary DNA sequence.

* * * * *

SEQUENCE LISTING

<160> NUMBER OF SEQ ID NOS: 2

<210> SEQ ID NO 1
<211> LENGTH: 75
<212> TYPE: DNA
<213> ORGANISM: Artificial
<220> FEATURE:
<223> OTHER INFORMATION: Randomly generated exemplary sequence for
      demonstrating technique
<220> FEATURE:
<221> NAME/KEY: misc_feature
<222> LOCATION: (64)..(65)
<223> OTHER INFORMATION: n is a, c, g, or t

<400> SEQUENCE: 1
aatgccttag gccatcgatg atatatacga tcgcgatgct gacggcgcga tcattataca    60
tcannagtag ctaat                                                    75

<210> SEQ ID NO 2
<211> LENGTH: 66
<212> TYPE: DNA
<213> ORGANISM: Artificial
<220> FEATURE:
<223> OTHER INFORMATION: Randomly generated exemplary sequence for
      demonstrating technique

<400> SEQUENCE: 2
ttcctgaatc cggtagctac tcgatattct agcgcaacgc ccactgcact agtaatatgt    60
agtagt                                                              66